United States Patent [19]

Tomaru

[11] Patent Number: 5,595,974
[45] Date of Patent: Jan. 21, 1997

[54] MEDICAMENTS FOR THE TREATMENT OF RESTENOSIS AND ARTERIAL SCLEROSIS

[75] Inventor: Takanobu Tomaru, Tokyo, Japan

[73] Assignee: Tobishi Pharmaceutical Co., Ltd., Tokyo, Japan

[21] Appl. No.: 555,451

[22] Filed: Nov. 9, 1995

[30] Foreign Application Priority Data

Dec. 26, 1994 [JP] Japan ................................ 6-322011
[51] Int. Cl.$^6$ .................................................. A61K 38/00
[52] U.S. Cl. ........................ 514/21; 514/822; 514/824
[58] Field of Search ............................ 514/21, 822, 824

[56] References Cited

PUBLICATIONS

Journal of Biological Chemistry, vol. 262, No. 7, pp. 3132–3135, Mar. 5, 1987, N. Itoh, et. al., "Molecular Cloning and Sequence Analysis of cDNA for Batroxobin, A Thrombin–like Snake Venom Enzyme".

Medicine and Pharmacy, vol. 14, No. 4, pp. 1061–1071, Oct. 1985, Shizen Kagakusha.

Merck Index, 11th Ed., 1989, #1020, #4571.

*Primary Examiner*—Kimberly Jordan
*Attorney, Agent, or Firm*—Oblon, Spivak, McClelland, Maier & Neustadt, P.C.

[57] ABSTRACT

A medicament for the treatment and/or prophylaxis of restenosis and arterial sclerosis after percutaneous transluminal angioplasty, characterized in that the medicament contains batroxobin as an effective component.

6 Claims, No Drawings

MEDICAMENTS FOR THE TREATMENT OF RESTENOSIS AND ARTERIAL SCLEROSIS

BACKGROUND OF THE INVENTION

The present invention relates to a medicament for the treatment and/or prophylaxis of restenosis and arterial sclerosis after percutaneous transluminal angioplasty, which contains batroxobin as an effective component.

It has been considered that intima pachymenia in the wall of blood vessel after the percutaneous transluminal angioplasty which has been extended as a method for treating of arteriosclerotic intima pachymenia, myocardial infarction and angina pectoris is caused by endotherial injury of blood vessel, and it has been reported that intima pachymenia will be formed in such a process that smooth muscle cell wanders from media of blood vessel and repeats its proliferation in the intima.

However, this phenomenon has hardly been elucidated physiologically and pharmacologically. Although it has been known that platelet-derived growth factor (PDGF) has an action for accelerating wandering of smooth muscle cell and its proliferation, there are no reports confirming that only the factor is directly involved in arteriosclerotic intima pachymenia or re-pachymenia after percutaneous transluminal angioplasty.

Thus, there has not been found such a medicament and a method for treating intima pachymenia in the wall of blood vessel after the percutaneous transluminal angioplasty which has been extended as a method for treating of arteriosclerotic intima pachymenia, myocardial infarction and angina pectoris.

According to recent reports, the number of the percutaneous transluminal angioplasty conducted in Japan, for example PTCA (percutaneous transluminal coronary angioplasty) is reported to be about 35,000, and the incidence of restenosis caused by intima pachymenia in the wall of blood vessel after the percutaneous transluminal angioplasty is to be from 20% to 50%. Hence, it is very important subjects to develop a medicament for the treatment and/or prophylaxis of the restenosis.

The inventors of this invention have conducted various studies to develop the medicament for treatment and/or prophylaxis of intima pachymenia in the wall of blood vessel by the use of an animal model. As a result, the inventors have found out that intima pachymenia in the wall of blood vessel can remarkably be inhibited by administering an effective amount of batroxobin.

SUMMARY OF THE INVENTION

It is an object of the present invention to provide an effective medicament for the treatment and/or prophylaxis of intima pachymenia in the wall of blood vessel after the percutaneous transluminal angioplasty which has been extended as a method for treating of arteriosclerotic intima pachymenia, myocardial infarction and angina pectoris.

The present invention provides a medicament for the treatment and/or prophylaxis of restenosis and arterial sclerosis after percutaneous transluminal angioplasty containing batroxobin as an effective component.

Since batroxobin exhibits species-specificity to manmalia, it is preferable to use optionally batroxobin together with heparin in manmalia of which the plasma fibrinogen concentration does not remarkably decrease upon administration of batroxobin.

Batroxobin used in the present invention is a thrombin-like enzyme derived from snake (*Bothrops atrox moojeni*) venom and its formulation is commercially available under batroxobin formulation from Tobishi Pharmaceutical Co., Ltd.

It has not been known that batroxobin employed in the present invention has an action of inhibition for intima pachymenia in the wall of blood vessel.

Overall primary structure of the amino acids of batroxobin employed in the present invention has already been determined [N. Itoh et al., J. Biol. Chem. 262 (7) 3132–3135, 1987].

Batroxobin is a kind of serine protease like thrombin and has a molecular weight close to that of thrombin. They decompose fibrinogen to release fibrinopeptide A. However, they are different from each other in that thrombin releases also fibrinopeptide B but batroxobin does not; and thrombin acts to various blood coagulation factors but batroxobin does not act to blood coagulation factors excepting fibrinogen.

Batroxobin employed in the present invention is used as an inhibitor for intima pachymenia in the wall of blood vessel, anti-arteriosclerosis agent and a medicament for the treatment and/or-prophylaxis of restenosis after the percutaneous transluminal angioplasty by the action of inhibition to the intima pachymenia in the wall of blood vessel.

The dosage of batroxobin employed in the present invention is dependent on symptom. In general, the dosage is in the range of from 1 to 20 batroxobin units (hereinafter, abbreviated as BU) for adult per day, although the dosage outside the above range can be used on symptom.

Batroxobin may be suitably diluted and administered in the form of drip or injection, intravenously or topically. The batroxobin unit described herein is a unit representing an enzymatic activity of batroxobin and such an activity that the coagulation of plasma is taken place in $19.0\pm0.2$ seconds when 0.1 ml of a batroxobin solution is added to 0.3 ml of standard human plasma containing citric acid at a temperature of 37° C. is defined as 2 BU.

DESCRIPTION OF THE PREFERRED EMBODIMENTS

The present invention will hereunder be described in more detail with reference to the following Examples.

EXAMPLE

The components and their contents in 1 ml of batroxobin formulation [a thrombin-like enzyme derived from snake (*Bothrops atrox moojeni*) venom] are as follows:

| | |
|---|---|
| batroxobin (main component) | 10 BU |
| chlorobutanol (preservative) | 3 mg |
| gelatin hydrolyzate (stabilizer) | 0.1 mg |
| sodium chloride (isotonic agent) | 9 mg |
| distilled water for injection | to 1 ml |

[Test]

Common iliac arteries of high cholesteric rabbits to which a diet containing 2% of cholesterol was loaded for a month were used as a model of the restenosis wherein the model consists of the heparin group with seven male rabbits and the batroxobin combined with heparin group with seven male rabbits, weighing between 2.5 kg and 3 kg, respectively.

This model has been most often used whereby many observations have been obtained and hence were used as a model of restenosis after percutaneous transluminal angioplasty of arterial sclerosis in the test. More specifically, a catheter sheath was inserted into femoral artery of the rabbit and then common iliac artery was injured by advancing balloon catheter through the catheter sheath to the common iliac artery. After the common iliac artery was injured, the balloon catheter was further advanced to bifurcation of aorta. After 2 ml of saline was locally injected through the sheath while occluding a proximal portion by inflating the balloon catheter, the blood perfusion was restarted. This is referred to as a control side.

On the other hand, similarly, 2 ml of saline containing heparin (25 U/kg) or a mixed solution of batroxobin formulation (1 BU/kg) and heparin (25 U/kg), that is, 2 ml of saline in which batroxobin and heparin were mixed at the weight ratio of 1:100 was locally injected into the injured common iliac artery and after retaining the state for 3 minutes, the blood perfusion was restarted. This is referred to as a drug administered side.

The observation by angioscope and angioscopic visualization after one hour showed the presence of occlusive thrombus or mural thrombus on the control side of all animals but did not show the presence of occlusive thrombus on the drug administered side.

Post-operatively, the percent luminal obstruction (%) of both the control side and the drug administered side were compared by continuing the load of high cholesterol for one month. That is, effects for preventing stenosis by local administration of batroxobin was evaluated by angioscopic visualization after one month from vasucular injury to compare the percent luminal obstruction (%) caused by intima pachymenia.

The control side to which only saline was administrated showed higher percent luminal obstruction (%) by angioscopic visualization after one month and the formation of stenosis in common iliac artery by loading high cholesterol. The drug administrated side to which batroxobin and heparin were administered showed remarkably reduced percent luminal obstruction (%) as compared with the group to which only heparin was administered (P<0.05).

The results are shown in the following table.

TABLE

| | Percent luminal obstruction (%) | | |
|---|---|---|---|
| | Control side | Drug administered side | |
| Heparin group | 73 ± 17 | 34 ± 31 | (n = 7, P < 0.01) |
| Batroxobin + heparin group | 59 ± 39 | 5 ± 5 | (n = 7, P < 0.05) |

The percent luminal obstruction (%) was calculated by the following equation:

Percent luminal obstruction $$(\%) = 100 \times [((①+②)/2 = ③)/[(①+②)/2]$$

①: Inner diameter of blood vessel near stenosis (proximal portion)

②: Inner diameter of blood vessel near stenosis (distal portion)

③: Minimum inner diameter of blood vessel on stenosis.

As shown in the results, the combination of batroxobin and heparin exhibited the effects for preventing restenosis. However, the use of heparin is not always necessary.

The defibrinogenating action of batroxobin to plasma fibrinogen in a rabbit is significantly lower than that of human-fibrinogen ("Medicine and Pharmacy", Mitsuoki Ohba et al., Vol. 14, No. 4, p. 1061–1071, 1985.10, Shizen Kagakusha, Tokyo, Japan).

Therefore, heparin was used with batroxobin in the test for preventing reocclusion caused by early forming of thrombus by platelet.

Acute toxicity test for batroxobin was conducted by intravenous administration to mice, rats, rabbits and dogs. The resulted LD, 0 values (BU/kg) were as follows:

| | $LD_{50}$ value (BU/kg) |
|---|---|
| mice (ddY strain) | 192–210 |
| rats (Wistar strain) | 105–110 |
| rabbits (NW species) | >300 |
| dogs (hybrid) | 190–208 |

Batroxobin used in the present invention prevents thrombus formation, inhibits intima pachymenia in the wall of blood vessel and is effective for the treatment and/or prophylaxis of restenosis and arterial sclerosis after percutaneous transluminal angioplasty.

Whereas particular embodiments of the invention have been described above for purposes of illustration, it will be appreciated by those skilled in the art that numerous variations of the details may be made without departing from the invention as described in the appended claims.

What is claimed is:

1. A method for the treatment or prophylaxis of restenosis and arterial sclerosis after percutaneous transluminal angioplasty, which comprises administering an effective amount of batroxobin to a patient in need thereof.

2. The method of claim 1, wherein heparin is used in combination with batroxobin.

3. The method of claim 2, wherein batroxobin and heparin are used in a weight ratio of about 1:100.

4. The method of claim 1, wherein batroxobin is a thrombin-like enzyme derived from the venom of *Bothrops atrox moojeni*.

5. The method of claim 1, wherein from about 1 to 20 batroxobin units are administered per day to said patient.

6. The method of claim 1, wherein said batroxobin is administered by injection.

* * * * *